(12) United States Patent
Mack

(10) Patent No.: US 7,048,539 B2
(45) Date of Patent: May 23, 2006

(54) ANATOMICAL TRANSFER BOW WITH LEVELING DEVICE

(75) Inventor: Heinz Mack, Munich (DE)

(73) Assignee: Sam Prazisionstechnik, Gauting (DE)

( * ) Notice: Subject to any disclaimer, the term of this patent is extended or adjusted under 35 U.S.C. 154(b) by 148 days.

(21) Appl. No.: 10/227,390

(22) Filed: Aug. 26, 2002

(65) Prior Publication Data

US 2003/0059739 A1 Mar. 27, 2003

(30) Foreign Application Priority Data

Aug. 29, 2001 (DE) ............... 101 42 139

(51) Int. Cl.
*A61C 19/04* (2006.01)
(52) U.S. Cl. ....................... 433/73
(58) Field of Classification Search .......... 433/68, 433/69, 72, 73, 57, 54, 56; 33/512, 513, 33/54, 333, 334, 276, 277
See application file for complete search history.

(56) References Cited

U.S. PATENT DOCUMENTS

| 3,218,716 | A |   | 11/1965 | Stuart |
| 5,738,517 | A | * | 4/1998 | Keller ......................... 433/73 |
| 6,109,917 | A | * | 8/2000 | Lee et al. .................... 433/73 |
| 6,152,732 | A | * | 11/2000 | Lindekugel ................. 433/73 |

FOREIGN PATENT DOCUMENTS

| DE | 3347830 | 3/1985 |
| DE | 19534991 | 4/1997 |
| DE | 19702840 | 7/1998 |

* cited by examiner

*Primary Examiner*—Melba N. Bumgarner
(74) *Attorney, Agent, or Firm*—William E. Jackson; Stites & Harbison PLLC

(57) ABSTRACT

An anatomical transfer bow is made available which consists principally of a central part, with two pivotable side arms connected via a pivot point, of the nasion support with mounting part and nose roll, and of the bite-fork carrier with bite fork. The anatomical transfer bow also has a leveling device for aligning the transfer bow with the interpupillary line.

2 Claims, 2 Drawing Sheets

ANATOMICAL TRANSFER BOW WITH LEVELING DEVICE

Figure 1:
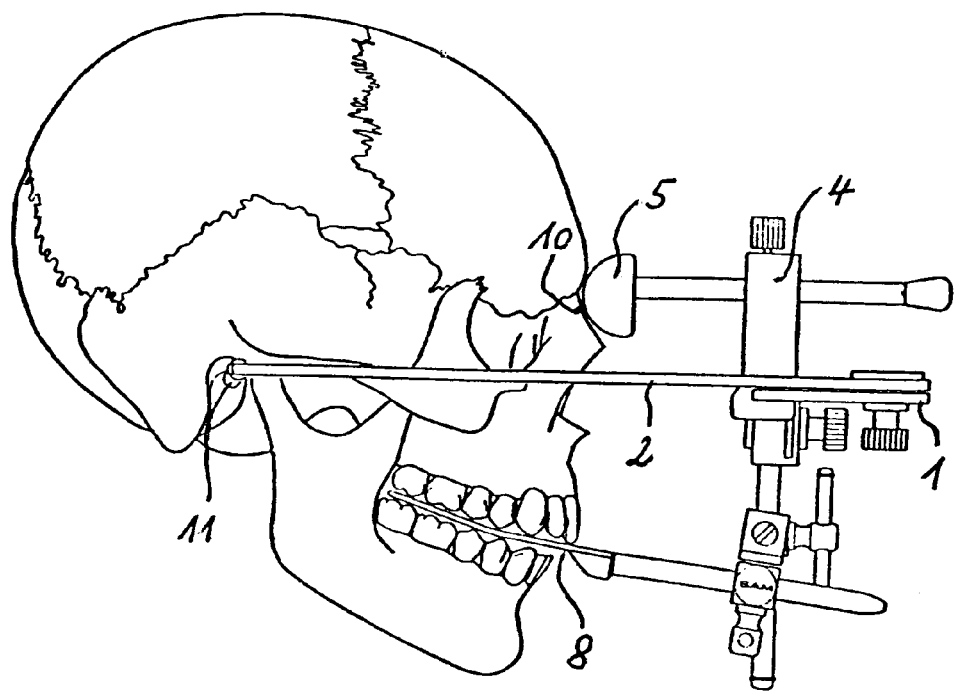

The present invention relates to an anatomical transfer bow consisting principally of a central part, with two pivotable side arms connected via a pivot point, of the nasion support with mounting part and nose roll, and of the bite-fork carrier with bite fork.

The Applicant has been manufacturing and marketing an anatomical transfer bow of this kind for years now. Its structure can be seen from attached FIGS. 1 to 3.

An anatomical transfer bow which is in principle similar was described in U.S. Pat. No. 3,218,716 (Stuart) published in 1965.

The anatomical transfer bow is used to transfer the reference plane (which is formed by the imaginary linear connection of three anatomical reference points at the base of the patient's skull) from the patient to the articulator in order in this way to position the jaw models, produced by impressions, in the articulator (simulator) in a manner which is correct in relation to the skull, i.e. with the correct coordinates in respect of the skull. Only in this way is it possible to correctly simulate the functions of the movable lower jaw in relation to the upper jaw which is fixed relative to the lower jaw. The three anatomical reference points are defined by the two external auditory canals and the nasion.

Models mounted in the articulator with the correct orientation with respect to the skull are thus an important tool in diagnosis and therapy. The correct spatial relationship of the model to the reference plane is a prerequisite for setting the occlusion plane, the condyle path angles, according to mean values and in particular for mounting with centric register.

The Frankfort horizontal plane (FH) represents, in conjunction with the nasion reference point, the universal spatial reference plane of upper jaw and lower jaw of the patient and of the models in the articulator. The reference points of the Frankfort horizontal plane are the highest points of the two external auditory canals (the poria) and the lowest point of the bony framework of the orbit (the orbitale).

The bite-fork carrier remains symmetrically positioned by means of optimized pivot points of the pivotable side arms of the anatomical transfer bow. The bite-fork carrier preferably consists of a three-dimensionally adjustable mechanical connection of rods and clamps, in particular of a cardan joint.

The nose roll of the nasion support, lying on the bridge of the nose serving as reference point, ensures that the anatomical transfer bow lies exactly at the orbitale of the patient. By means of the two ear inserts located on the transfer bow, the anatomical transfer bow is located on the porion reference points (porion is the highest point of the external auditory canal) which, as has already been mentioned, form, together with the nasion reference point, the reference plane which is to be transferred when these points are connected linearly.

For esthetic reasons, it is a requirement in dentistry that the line of the cutting edges of the teeth of the upper jaw lies parallel to the line connecting the midpoints of the pupils (interpupillary line) and that the upper jaw model obtained from taking an impression of the upper jaw is transferred in the same (correctly coordinated) position from the skull to the articulator. The interpupillary line can be seen in FIG. 2.

When applying the anatomical transfer bow to the three reference points (the two external auditory canals and the nasion), a disadvantage has been found to be that, because of the soft tissues lying at the three anatomical reference points, deviations from the interpupillary line occur. However, deviations also occur as a result of unequal positioning or unequal finger pressure by operator and/or patient and these deviations make it necessary to readjust the equipment. For this reason, an exact alignment (leveling) of the anatomical transfer bow with the interpupillary line is necessary to ensure that the position of the upper jaw model correlates with respect to the base of the skull (reference plane).

It is therefore an object of the present invention to make available a device by means of which the deviations when applying the transfer bow can be corrected in a straightforward manner.

According to the present invention, this object is achieved by the fact that the anatomical transfer bow also has a leveling device for aligning the anatomical transfer bow with the interpupillary line.

With this levelling device (levelling aid) additionally arranged on the anatomical transfer bow, it is possible for the anatomical transfer bow, which is fitted in the two external auditory canals and lies on the nasion, to be readjusted in a simple and reproducible manner with reference to the interpupillary line (precision adjustment).

The leveling device is preferably a sighting pin which protrudes, parallel to the central part, on both sides of the mounting part of the nasion support.

However, the leveling device can also consist of sighting indicator or spacer which are arranged directly on the central part or side arms of the anatomical transfer bow and which can if appropriate be adjusted steplessly in height and can additionally be connected to one another at their upper ends by way of a filament or rod extending parallel to the interpupillary line.

The invention is explained with reference to FIGS. 1 to 3, which are self-explanatory, but without thereby limiting the invention. All of the details shown in the figures belong to the disclosure of the present invention.

Figure 2:
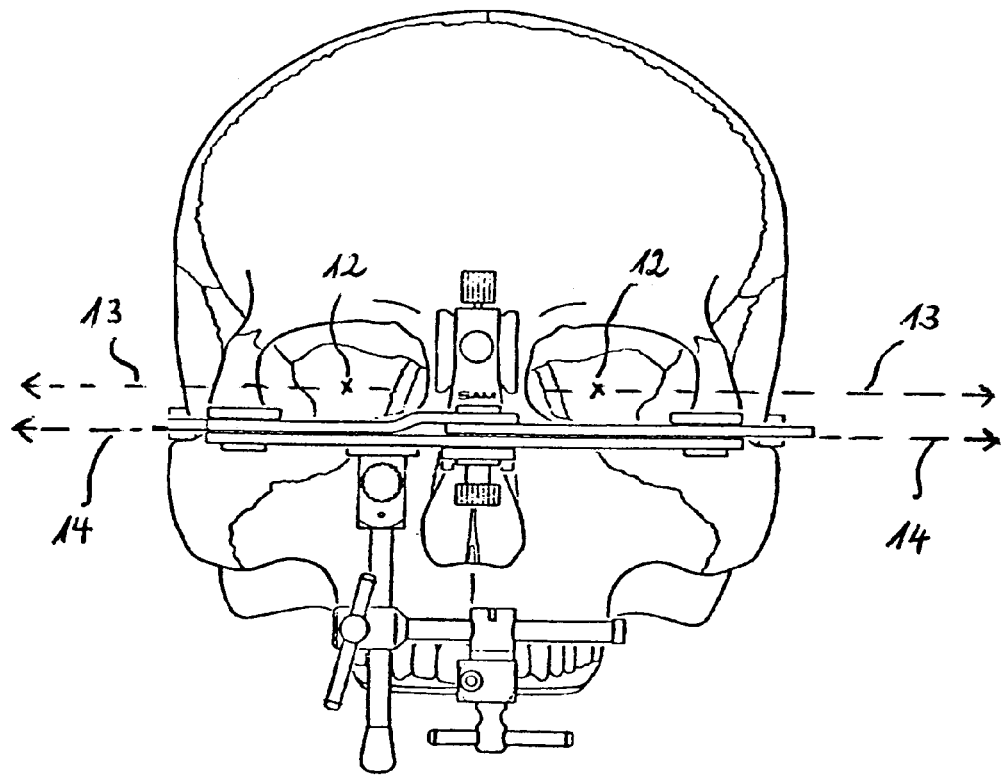
Figure 3:
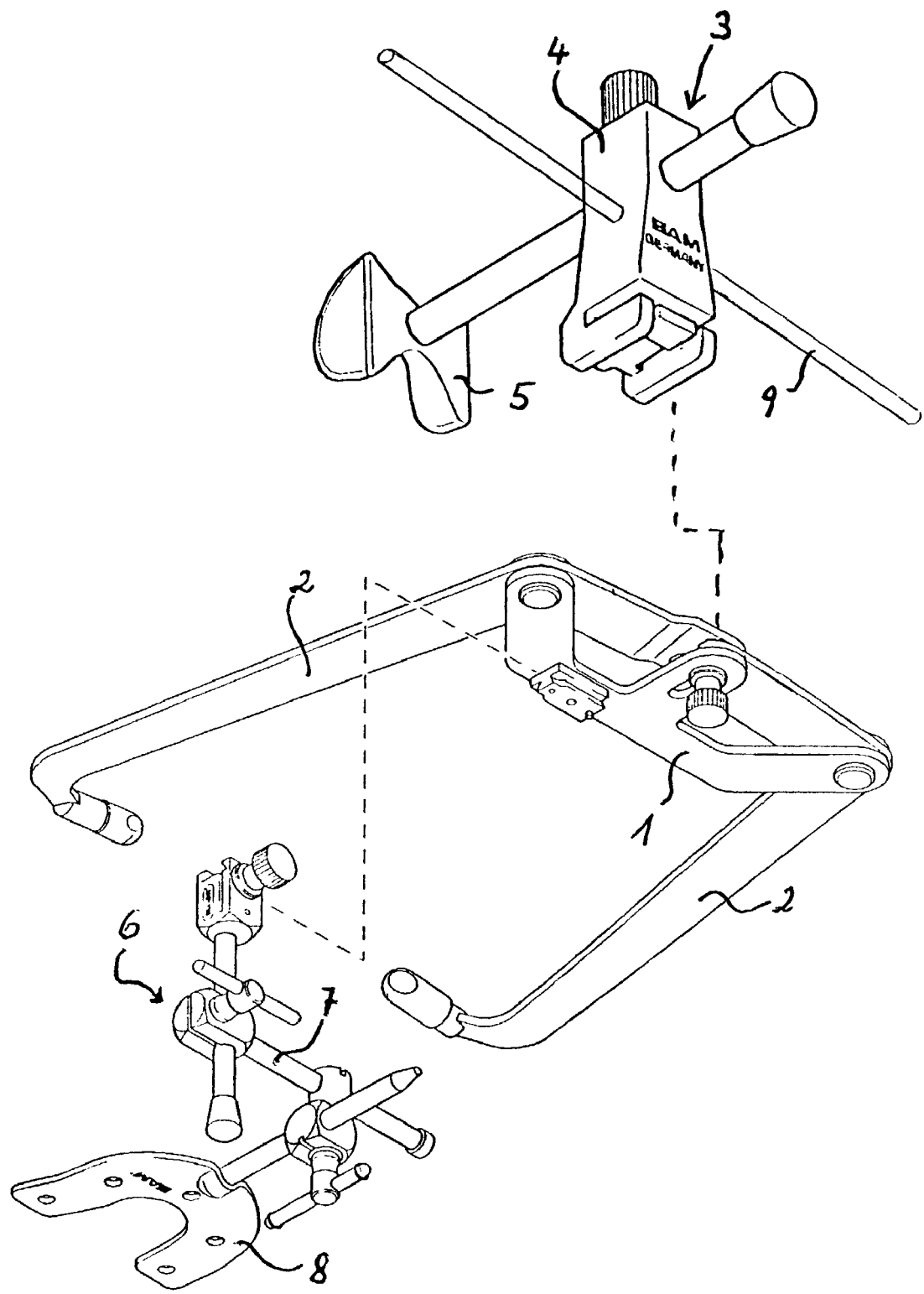

The reference numbers used in FIGS. 1 to 3 have the following meanings:

1 central part of the transfer bow
2 side parts of the transfer bow
3 nasion support
4 mounting part of the nasion support
5 nose roll
6 bite-fork carrier
7 three-dimensionally adjustable mechanical connection
8 bite fork
9 sighting pin
10 nasion
11 porion
12 pupil midpoints
13 interpupillary line
14 parallel line of the transfer bow to the interpupillary line FIG. 1 shows, in diagrammatic representation, a side view of a human skull on which an anatomical transfer bow has been placed, with the corresponding reference numbers whose meanings are indicated above.

FIG. 2 shows, in diagrammatic representation, a front view of a human skull on which an anatomical transfer bow has been placed, with the corresponding reference numbers whose meanings are indicated above. The interpupillary line is shown by 13. With precision leveling, the operator brings the line 14 of the anatomical transfer bow parallel to the interpupillary line.

FIG. 3 shows the anatomical transfer bow with sighting pin 9 in a diagrammatic and partially exploded view, with the corresponding reference numbers whose meanings are indicated above.

What is claimed is:

1. In an anatomical transfer bow comprising a central part (1), two pivotable side arms (2) connected via a pivot point to said central part, a nasion support (3) having a mounting part (4) and nose roll (5), a bite-fork carrier (6), a bite fork (8), a three-dimensionally adjustable mechanical connection (7) between said bite fork (8) and said central part, the improvement wherein the anatomical transfer bow also has a leveling device for aligning the transfer bow with the interpupillary line of a person, said leveling device is a sighting pin (9) which protrudes, parallel to the central part (1), from both sides of the mounting part (4) of the nasion support (3).

2. An anatomical transfer bow comprising:
a central part; two pivotable side arms connected via respective pivot points to said central part;
a nasion support with a mounting part attached to said central part;
a nose roll attached to said nasion support;
a bite fork carrier and a bite fork with a three dimensionally adjustable mechanical connection to said central part and said bite fork, and
said anatomical transfer bow having an anatomical and non-horizon oriented related means for aligning the transfer bow parallel with the interpupillary line of a person, said means for aligning comprises a sighting pin which protrudes on both sides of said mounting part of said nasion support, and said sighting pin is parallel to the axis of said central part and side arms of the transfer bow.

* * * * *